United States Patent [19]

Imaizumi

[11] 4,182,914

[45] Jan. 8, 1980

[54] PROCESS FOR CONTINUOUSLY PRODUCING DIISOPROPYL ETHER

[75] Inventor: Masao Imaizumi, Tokyo, Japan

[73] Assignee: Nippon Oil Company Limited, Tokyo, Japan

[21] Appl. No.: 865,430

[22] Filed: Dec. 29, 1977

Related U.S. Application Data

[63] Continuation-in-part of Ser. No. 689,010, May 24, 1976, abandoned, which is a continuation-in-part of Ser. No. 435,566, Jan. 22, 1974, abandoned.

[51] Int. Cl.$^2$ .................... C07C 41/06; C07C 41/10
[52] U.S. Cl. ................................................ 568/697
[58] Field of Search ................ 260/614 A, 614 R; 568/697

[56] References Cited

U.S. PATENT DOCUMENTS

| 2,067,385 | 1/1937 | Evans et al. | 260/614 A |
|---|---|---|---|
| 2,391,084 | 12/1945 | Carmody | 260/614 A |
| 2,922,822 | 1/1960 | Brach | 260/614 A |
| 2,994,720 | 8/1961 | Hakala et al. | 260/614 A |

FOREIGN PATENT DOCUMENTS

| 2403196 | 8/1974 | Fed. Rep. of Germany | 260/614 A |
|---|---|---|---|
| 7704558 | 11/1977 | Netherlands | 260/614 A |
| 957000 | 4/1964 | United Kingdom | 260/614 A |

*Primary Examiner*—Howard T. Mars
*Attorney, Agent, or Firm*—Holman & Stern

[57] ABSTRACT

There is disclosed a process for continuously producing diisopropyl ether of high purity from isopropyl alcohol and propylene at a high yield, which comprises the steps of: continuously passing isopropyl alcohol and propylene at a given molar ratio through a first fixed bed filled with particles of strongly acidic cation-exchange resin at a temperature in the range from 100° C. to 130° C.; then passing the reaction mixture through a second fixed bed filled with a water-insoluble, solid, particulate acid-neutralizing agent; and flash-removing unreacted propylene from the mixture, followed by solvent refining and distillation, whereby diisopropyl ether of high purity is continuously obtained at a high yield.

4 Claims, 1 Drawing Figure

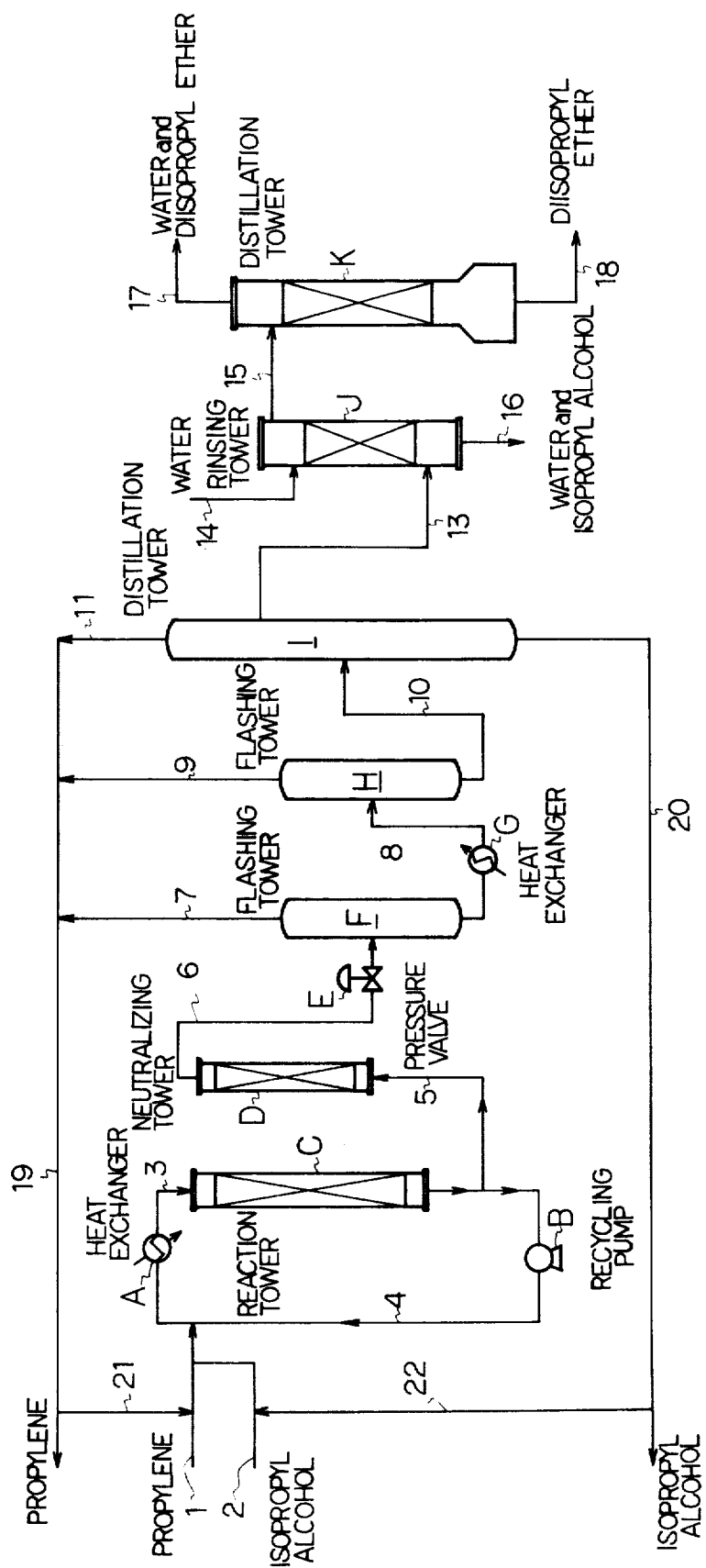

PROCESS FOR CONTINUOUSLY PRODUCING DIISOPROPYL ETHER

CROSS REFERENCE TO RELATED APPLICATION

This application is a Continuation-in-Part application of my Application Ser. No. 689,010 filed May 24, 1976, which is a Continuation-In-Part application of Application Ser. No. 435,566 filed Jan. 22, 1974 both now abandoned.

BACKGROUND OF THE INVENTION

This invention relates to a process for producing diisopropyl ether of high purity from isopropyl alcohol and propylene continuously with high yield.

In the prior art processes, it has been a common practice to separate and purify diisopropyl ether obtained as a by-product when isopropyl alcohol is produced by hydrating propylene. However, the following drawbacks have been encountered with those processes. First, production of diisopropyl ether is subject to restriction by the rate of formation of the by-product upon the production of isopropyl alcohol. Second, the by-product obtained is a mixture of diisopropyl ether and other substances which obstruct the separation and purification of diisopropyl ether, so that it is difficult to purify the diisopropyl ether mixture. Furthermore, where the indirect hydrating process is used in which sulfuric acid is used as a catalyst for the production of isopropyl alcohol, installations used suffer from severe corrosion.

Heretofore, a process is disclosed, for example, in U.S. Pat. No. 2,067,385 issued to Evans, in which ether is prepared from secondary base olefin and aliphatic alcohol in the presence of sulfuric acid as a catalyst. Since $H_2SO_4$ is used as a catalyst, however, the process has been attended with the following drawbacks:

1. Installations used suffer from severe corrosion.
2. Where olefin of a small carbon number such as propylene is used, there is produced an ether which is easily soluble into a layer of $H_2SO_4$, with the result that ether thus produced is difficult to be separated from the $H_2SO_4$. In addition, there arises the necessity of adding much water to the reaction mixture prior to the heating and isolation of ether, e.g. isopropyl ether because the direct heating of the concentrated sulfuric acid-ether mixture causes the reverse reaction in which the ether is decomposed. Thus, the $H_2SO_4$ catalyst cannot be directly reused. For reusing the catalyst reconcentration is required.
3. As a substantial quantity of waste sulfuric acid is produced in the concentration of the catalyst for recovery, water is contaminated.

Because of these drawbacks as described, it has been found that the process for synthesizing diisopropyl ether by using concentrated sulfuric acid is not practically usable.

The above-described U.S. patent teaches, besides the use of sulfuric acid, the use of catalyst in the form of solid, such as (1) phosphoric acid, esters of sulfuric acid, (2) $POCl_3$, boron halides, $AlCl_3$, $FeCl_3$, (3) $Al_2(SO_4)_3$, $MgCl_2$, $KHSO_4$, $NaHSO_4$, potash alum, acid salt, (4) active charcoal, silica gel, kieselguhr, kaolin and aluminum silicate.

From the fact that Evans describes in page 2, left column, lines 3 through 6 of the specification that $H_2SO_4$ is preferable as a catalyst, it will be seen that the above group (1) would not be industrially effective for the same reason as discussed above in connection with disadvantages of sulfuric acid.

The compounds of Group (2), the so-called Friedel-Crafts compounds, have a fairly high acidity so that they have similar properties to concentrated sulfuric acid as far as corrosion is concerned. These metal halides are hygroscopic and are very reactive with water so that they are decomposable due to the remaining moisture even if apparently dry. Any of the decomposition products are so corrosive as to erode every portion of the apparatus. Furthermore, as these compounds absorb moisture from the air, they are troublesome in handling and are disadvantageous in industrial application.

The compounds of Group (3) are salts which are hygroscopic and have drawbacks similar to those as mentioned above. In fact, the reactivity is not improved even if $Al_2(SO_4)_3$, for example, is employed as the catalyst.

The compounds in Group (4) are solid materials similarly to the acidic cation exchange resins of the present invention. These compounds as such may be usable as a particulate material for the reaction layer of fixed bed. However, even if they are actually used for the reaction of ispropyl alcohol with propylene, it will be evident that the reaction would hardly occur or, if any be actuated with lowest activity.

In fact, the Evans patent does not teach concretely the art of producing ether of high purity efficiently by using any of these compounds in the form of a solid.

Alternatively, British Pat. No. 957,000 teaches the art of synthesizing ter-butyl-alkyl ether from isobutylene and alcohol by using a cation-exchange resin. This British patent, however, discloses only the reaction between isobutylene and alcohol at a low temperature ranging from 0° to 100° C., preferably from 20° to 80° C. What is taught by said British patent is the case where a tertiary olefin such as isobutylene is used as the olefin, rather than the case where a secondary base olefin such as propylene is employed. The British patent discloses on lines 9 through 14 at page 2 in the specification that isobutylene has a reactivity which is many times greater than the reactivity of an olefin such as propylene. Such description would be interpreted as making a denial of the use of propylene as an olefin in the production of diisopropyl alcohol on an industrial scale, rather than as implying the possibility of the use of proplyene as olefin therefor.

OBJECTS AND SUMMARY OF THE INVENTION

An object of the present invention is to provide an improved process for continuously, producing diisopropyl ether of high purity from isopropyl alcohol and propylene at high yield.

Another object of the invention is to provide an improved process for continuously producing diisopropyl ether at a high yield on an industrial scale.

Still another object of the invention is to provide an improved process for continuously producing diisopropyl ether wherein installations used are free of being severely corroded.

A still further object of the invention is to provide an improved process for continuously producing diisopropyl ether without the need for glass-lined installations.

The other objects of the invention will become apparent from the following description.

According to the invention there is provided an improved process for continuously producing diisopropyl ether of high purity from isopropyl alcohol and propylene at a high yield. The improved process comprises the steps of passing continuously isopropyl alcohol and propylene at a molar ratio of 1:0.5 to 1:3, of isopropyl alcohol to propylene, through a first fixed bed filled with particles of strongly acidic cation-exchange resin having a mean grain diameter of 0.5 to 10 mm at a liquid space velocity of 0.2 to 2 (1/hr) at a temperature from over 100° C. to 130° C. at a pressure ranging from 20 to 50 atmospheres to react with each other, dividing the resultant reaction mixture emerging from said first fixed bed into first and second streams, passing said first stream through a second fixed bed filled with a water-insoluble, solid, particulate, acid-neutralizing agent having a mean grain diameter of 0.1 to 10 mm, at a temperature ranging from 20° to 130° C., said acid-neutralizing agent being selected from the group consisting of magnesium oxides, aluminium oxides, magnesium-aluminium double oxides and hydrates thereof, and complex oxides and hydrates of Mg and/or Al with at least one element selected from Na, K, C, Si, Ca, Ba and Sr, recycling said second stream to said first fixed bed filled with said cation-exchange resin, introducing the resultant neutralized mixture from said second fixed bed into a flashing tower and flashing the mixture to remove unreacted propylene from said mixture, distilling the flashed mixture in a multi-stage distillation tower to recover unreacted isopropyl alcohol from the bottom of said distillation tower and obtain an azeotropic mixture of isopropyl alcohol and diisopropyl ether from an upper portion of said distillation tower, bringing said azeotropic mixture of isopropyl alcohol and diisopropyl ether into contact with a solvent selected from the group consisting of hydrocarbons, water and lower alcohols having from 1 to 4 carbon atoms, thereby separating said azeotropic mixture into a layer of isopropyl alcohol and a layer of diisopropyl ether, said layer of isopropyl alcohol containing said solvent when said solvent is water or the lower alcohol, and said layer of diisopropyl ether containing said solvent when said solvent is hydrocarbons, separating said layers and distilling said layer of diisopropyl ether, whereby diisopropyl ether of high purity is obtained.

DESCRIPTION OF THE INVENTION

In the process of the present invention, isopropyl alcohol and propylene are used as starting materials. As isopropyl alcohol, there may be used isopropyl alcohol commercially available in the market, preferably containing less than 1% by weight of moisture. Propylene should preferably be of high purity, but may contain less than 50% by weight of propane.

Isopropyl alcohol and propylene are heated to a temperature in the proximity of a reaction temperature separately or in a mixed condition and then introduced into a catalyst bed consisting of a strongly acidic cation-exchange resin. The isopropyl alcohol and propylene are fed at a molar ratio of 1:0.5 to 1:3 of isopropyl alcohol to propylene, preferably at a ratio of 1:1 to 1:2. In the case where the propylene value is less than 0.5, there results an increase in undesirable subsidiary reactions such as dehydration of isopropyl alcohol as well as an increase in the quantity of unreacted isopropyl alcohol. Where the propylene value is in excess of 3, an increased quantity of unreacted propylene results, thus imposing an increased burden on the refining step. In addition, an increased quantity of dimer of propylene is produced according to the subsidiary reaction.

Representative of the strongly acidic cation-exchange resin herein referred to are the sulfonic acid type resin derived from styrene, phenolsulfonic acid type resin and the like. The sulfonic acid type ion exchange resin derived from styrene is obtained by copolymerizing styrene with a polyunsaturated compound such as divinylbenzene to thereby yield a resin and then sulfonating the resin thus obtained. The sulfonated resin is ordinarily represented by the following formula:

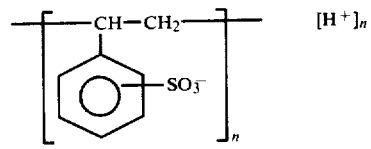

The phenolsulfonic acid type resin is ordinarily a condensate of phenolsulfonic acid with formaldehyde and is represented by the following formula:

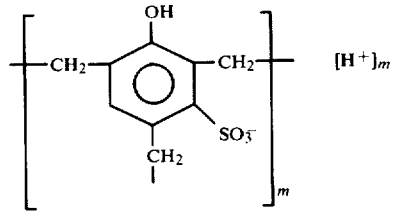

In the process of the present invention, the aforesaid strongly acidic cation-exchange resin is used as a catalyst in the form of a spherical or column-shaped particle having a mean grain diameter of 0.5 to 10 mm.

The particles of catalyst are charged in a pressure-resistant, cylindrical container, thereby forming a fixed bed.

The size of the fixed bed is optional and ordinarily ranges from 0.3 to 10 m in height. It is possible to use a plurality of fixed beds arranged in series or parallel relation to one another. Isopropyl alcohol and propylene are continuously fed to the fixed bed through the top end or bottom end thereof, preferably through the top end. The quantity of isopropyl alcohol and propylene being fed should give a liquid space velocity in the range of 0.2 to 2

$$( \frac{m^3}{m^3} \times \frac{1}{hr} = \frac{1}{hr} ),$$

preferably in the range of 0.5 to 1.5 1/hr.

The liquid space velocity herein referred to is the sum in volume (m$^3$) of isopropyl alcohol and propylene, both fresh and as recovered for reuse in the refining step, which are to be fed in liquid form to the fixed bed per cubic meter of catalyst per hour, the volume being defined at a temperature of 20° C. and a pressure of 10 kg/cm$^2$.

Since the reaction temperature according to the process of the present invention is specified to be a temperature higher than a critical temperature for propylene, determination of the phase of materials existing in the reacting conditions (i.e., liquid or gas phase) is so complicated and unclear in strict sense, so that a quantity of starting materials being fed is determined on the basis of the conditions at 20° C., and 10 kg/cm².

Inactive solvent might be possibly used for reaction of the starting materials, but the use of such inactive solvent is not desirable in the process of the present invention.

If the quantity of starting materials being fed is below 0.2 (1/hr) in liquid space velocity, the reaction between the materials progresses to satisfaction, but a reduced quantity of product results, this being disadvantageous from the viewpoint of production on an industrial basis. In addition, decomposition of the diisopropyl ether produced is accelerated. If the quantity of starting materials being fed exceeds 2 (1/hr), then insufficient reaction results, thus imposing an increased burden on the succeeding refining step.

In the process of the present invention, isopropyl alcohol and propylene are passed through the first fixed bed and the resultant mixture leaving the fixed bed is divided into two streams, one stream being fed to a succeeding fixed bed of acid-neutralizing agent, and the other stream being recycled to the first fixed bed of cation-exchange resin. In this case, the ratio in quantity of a stream of fresh starting materials to the stream of the mixture to be recycled may preferably be from 1:3 to 1:10 by weight.

In this connection, the liquid space velocity indicating the quantity of starting materials being fed is independent of the quantity of the mixture which is to be directly recycled to the first reaction vessel.

The reasons why the recycle-feeding system is adopted in the process of the present invention are as follows. The reaction between isopropyl alcohol and propylene is exothermic, and because of the nature of the catalyst being used in the process of the present invention, it is mandatory to maintain the temperature in the reaction container constant. Particularly, a rise in temperature to over 130° C. must be absolutely avoided from the viewpoints of inhibiting subsidiary reaction and preventing deterioration of the catalyst. Unless the recycling system is employed, then the temperature difference between the exit and the entrance of the reaction vessel would increase, thus requiring the provision of a special cooling means for the reaction vessel. Even in the case where the cooling means is provided in the reaction vessel, there is occasionally experienced an undesirable temperature rise locally in the reaction container. This is probably due to the fact that heat transfer in a granular system is poor. The recycling system is completely effective in maintaining temperature in the reaction bed comparatively uniform.

The reaction pressure in the process of the present invention is maintained within the range of 20 to 50 atmospheres preferably within the range of 30 to 40 atmospheres. In the case of reaction pressure lower than 20 atmospheres, incomplete reaction will result. In the case of a reaction pressure higher than 50 atmospheres, then rigid, pressure-resistant devices as reaction vessels and their accessories are entailed, this being disadvantageous from economical and industrial aspects.

A reaction temperature in the process of the present invention falls within the range from over 100° C. to 130° C. In the case of a reaction temperature of 100° C. and below, reaction does not proceed sufficiently. In the case of a reaction temperature of over 130° C., there results in increased subsidiary reactions such as the dehydration of isopropyl alcohol and the dimerization of propylene. In addition, a large quantity of acidic material is effused from the strongly acidic cation-exchange resin used as the catalyst, and deterioration of the catalyst is accelerated.

In the process of the present invention, the presence of a cation-exchange resin as a catalyst makes it possible to obtain diisopropyl ether with high yield and to purify the resultant diisopropyl ether to a high degree. This is due to the fact that there occurs substantially no reaction other than theat represented by the following equation:

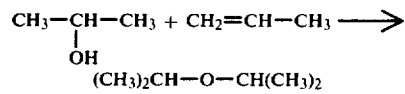

$$CH_3-\underset{\underset{OH}{|}}{CH}-CH_3 + CH_2=CH-CH_3 \longrightarrow$$
$$(CH_3)_2CH-O-CH(CH_3)_2$$

In other words, a large quantity of water, esters or polymer of olefins and the like does not exist in the reaction conditions. However, under some reaction conditions, it is impossible to completely prevent production of a small quantity of water (for example, in the order of 2% of water with respect to diisopropyl ether being produced), because of the following reactions.

IPA→propylene+H₂O

2IPA→IPE+H₂O, where IPA is isopropyl alcohol and IPE diisopropyl ether.

Furthermore, an undesirable phenomenon arises, in which a small quantity of material having strong acidity is eluted from the strongly acidic cation-exchange resin into the reaction mixture. Should the mixture having an acidic material admixed therewith be fed intact to the succeeding refining step for being subjected to distillation and heating (which is usually incident to the distillation) for separation of an unreacted material from the mixture as well as purification of the product to the maximum, there would result subsidiary reactions such as decomposition (reverse reaction) of the product, i.e., diisopropyl ether, dimerization and dehydration of unreacted material, i.e., isopropyl alcohol, with the result of production of undesirable by-products and hence leading to lowered yield. Moreover, the acidic materials thus eluted and a small quantity of water coact to seriously corrode every portion of the apparatus.

In order to remove the eluted strongly acidic material, it may be proposed to neutralize such a material with an aqueous solution containing a material having a strong basicity, such as NaOH, CaO or Ca(OH)₂. In such a case, however, separation of the salts produced by the neutralization reaction is difficult. In addition the concentration of the acidic material effused depends upon kinds of catalysts used, the reaction temperature, the flow rate of starting materials and the reaction time and so forth, thus making it difficult to control the quantity of basic material being added. If the quantity of base added is smaller than required, then insufficient removal of acidic material results, with the accompanying aforesaid drawbacks, while if an excess of base is fed, the succeeding refining treatment must be carried out under the conditions for treating the alkali material. Furthermore, where an unreacted material is recycled, the unreacted material being recycled is usually accompanied by strong alkali material, such that when such unreacted material is recycled intact to the first reaction means, then greatly lowered activity of the strongly acidic cation-exchange resin would result. For this reason, the unreacted material containing a strong alkali material cannot be reused for recycling, without being neutralized with acid. Thus, an additional acid-neutralizing step is required.

Furthermore, where the aforesaid NaOH or CaO is used in the form of a solid, since a small quantity of water is contained in the mixture obtained by reaction in the process of the present invention, the solid NaOH or CaO would be slowly dissolved during the continuous use thereof, with the accompanying drawbacks described above.

For removal of the acidic material eluted, it might be thought possible to use an absorbent such as activated carbon. This method, however, has the drawback that the adsorbing capacity of such an adsorbent is low and that if the concentration of acid to be adsorbed is lowered, the acid-adsorbing ability of the adsorbent is greatly lowered.

The process for producing diisopropyl ether continuously at high efficiency according to the present invention has another feature in that, to solve the above-described problem, and without the cited drawbacks, the mixture obtained by reaction is passed through a fixed bed filled with a water-insoluble, solid, particulate, acid-neutralizing agent having a mean grain diameter of 0.1 to 10 mm, so that both the mixture and the acid-neutralizing agent are brought into contact with each other.

The water-insoluble, solid, particulate, acid-neutralizing agent herein referred to is an inorganic solid particulate material which is extremely low in solubility in water (those having a solubility less than 0.1 g/100 g of water under the normal application conditions) and which have an acid-neutralization capacity of more than 1.0 m-mol/g.

The acid-neutralization capacity is determined by adding said solid material to an aqueous solution containing 1% by weight of $H_2SO_4$, allowing said acid aqueous solution to stand for 10 hours at 50° C., removing said solid material from said solution and calculating the number of m-mol of $H_2SO_4$ removed from said aqueous solution per gram of said solid material.

The water-insoluble, solid, particulate acid-neutralizing agents include magnesium oxides, aluminum oxides, magnesium-aluminum double oxides and hydrates thereof and complex oxides and hydrates of Mg and/or Al with at least one element selected from among Na, K, C, Si, Ca, Ba and Sr. Examples of such compounds are MgO, $MgO.mH_2O$ ($m=0$ to 0.5), $Al_2O_3$, hydrotalcite ($6MgO.Al_2O_3.CO_2.12H_2O$), $Al_2O_3.mSiO_2.nH_2O$ ($m=0.5$ to 3, $n=1$ to 6), $Al_2O_3.nH_2O$, ($n=1$ to 6), $2.5 MgO.Al_2O_3.nH_2O$ ($n=1$ to 6), $Na_2O.Al_2O_3.nH_2O$ ($n=1$ to 6) and $2MgO.6SiO_2.nH_2O$ ($n=1$ to 6).

Among these compounds, hydrotalcite and MgO are preferably used in the process of the present invention. Hydrotalcite herein referred to is usually approximately 3 in molar ratio of magnesium to aluminum. In case these are synthesized, there is obtained hydrotalcite having a molar ratio of magnesium to aluminum which covers a wide range, depending upon the production process. Some of the hydrotalcites having a molar ratio of magnesium to aluminum ranging from 1 to 10 show an X-ray diffraction diagram having a peak which features hydrotalcite whose molar ratio of magnesium to aluminum is approximately 3. Those which are in the range of 1 to 10 molar ratio of magnesium to aluminum are included in the hydrotalcites as referred to in the present invention, and which are effective for the purposes as described above.

The aforesaid solid, particulate, acid-neutralizing agent is used in the form of particles of spherical, flake- or columnar-shape having a mean grain diameter of 0.1 to 10 mm to form a fixed bed in the vessel.

The aforesaid mixture obtained by reaction is continuously passed through the fixed bed filled with the acid-neutralizing agent at a temperature ranging from 20° to 130° C. Where the temperature is lower than 20° C., incomplete removal of the acidic material results, and at the same time, there arises the necessity to cool the resultant mixture taken from the reaction container, thus resulting in loss of heat. A temperature of over 130° C. causes undesirable reactions such as decomposition of the reaction mixture and dehydration of the isopropyl alcohol. The temperature may preferably be in the range of 90° to 120° C. The quantity of the mixture which is passed through the fixed bed usually falls in a liquid space velocity range of 0.2 to 10 (1/hr).

In the process of the present invention, the mixture obtained by reaction is introduced into a flashing tower for being subjected to flashing treatment. The flashing tower is normally a multi-stage tower, in which a light weight compound containing essentially unreacted propylene is subjected to flashing for being removed from the mixture and discharged from the top of the tower. Two or three flashing towers may be arranged in series relation. Propylene thus separated from the mixture may be recycled to the first reaction container.

The mixture subjected to flashing is fed to a multi-stage distillation tower consisting of 10 to 40 stages. From the bottom of the distillation tower is recovered unreacted isopropyl alcohol. Isopropyl alcohol thus recovered may be recycled to the first reaction vessel. From the top of the distillation tower is recovered a small quantity of unreacted propylene, while from an upper portion of said distillation tower (a portion located at a level higher than the middle stage) is obtained an azeotropic mixture of isopropyl alcohol and diisopropyl ether or an azeotropic mixture of isopropyl alcohol, diisopropyl ether and $H_2O$. The azeotropic mixture herein referred to is a mixture containing isopropyl alcohol and diisopropyl ether at a ratio of 1:5.1 by weight and may include a mixture containing isopropyl alcohol and diisopropyl ether at a ratio of about 1:4.7 to 1:5.5. It is usual that a small quantity of water subsidiarily produced is contained in the azeotropic mixture. Thus, in the present invention, the small quantity of water is incorporated into the azeotropic mixture of isopropyl alcohol and diisopropyl ether and discharged together from the upper portion of the tower.

The azeotropic mixture is then brought into contact with a hydrophobic or hydrophilic solvent. A typical example of the hydrophobic solvent, includes hydrocarbons. In the case of a hydrocarbon solvent being used, the diisopropyl ether contained in the azeotropic mixture is separated from the mixture and removed to the solvent, whereby a layer of diisopropyl ether in solvent and a layer of isopropyl alcohol are formed.

A typical example of a hydrophilic solvent includes water or a lower alcohol normally having a carbon number of 1 to 4, such as methanol. In case a lower alcohol is used, it is the isopropyl alcohol which is separated from the azeotropic mixture and removed to the solvent, whereby a layer of isopropyl alcohol in a solvent and a layer of diisopropyl ether are formed in like manner. The quantity of solvent is normally in the range of 0.3 to 20 times by volume the quantity of azeotropic mixture.

In the process of the present invention, water is preferably used as the solvent. In this case, in order to hold the loss of diisopropyl ether to the minimum, the quantity of water may preferably be in the range of 0.5 to 50 times, most preferably, 0.5 to 3 times by volume the quantity of azeotropic mixture.

The layer of diisopropyl ether is then distilled to separate it from any solvent and from impurities whereby diisopropyl ether of high purity is obtained as a product.

BRIEF DESCRIPTION OF THE DRAWINGS

The single FIGURE is a flow sheet schematically showing the process of the present invention.

PREFERRED EMBODIMENT OF THE INVENTION

The process of the present invention will be referred to in detail with reference to the accompanying flow sheet.

Propylene which is a starting material is fed through line 1 and isopropyl alcohol, the other starting material is fed through line 2 for mixture with each other. The starting materials in the liquid phase join with fluid flowing through recycling line 4, then are heated in a heat exchanger A which is maintained at a desired reaction temperature, and introduced through line 3 into a reaction tower C, which contains a fixed bed of particles of a strongly acidic cation-exchange resin. Part of the fluid leaving the reaction tower C is recycled through line 4 by means of recycling pump B to join with the streams of fresh starting materials, thus being recycled to the reaction tower C. The remainder of the fluid leaving the reaction tower C is introduced through line 5 into a neutralizing tower D which contains a fixed bed of water-insoluble, solid particulate, acid-neutralizing agent. Fluid from the neutralizing tower D is introduced through line 6 into a first flashing tower F, and the pressure is reduced in the tower F. The pressure in the reaction towers C and D is controlled by a pressure valve E at a selected level. From the top of the flashing tower F, a gas consisting essentially of unreacted propylene is passed through line 7, while from the bottom of the tower F, liquid is taken out, and after having been cooled in a heat exchanger G, the liquid is introduced through line 8 into a second flashing tower H. From the top of the flashing tower H, a gas consisting essentially of pure propylene is discharged and passed through line 9, while liquid is taken from the bottom of the tower H and introduced through line 10 into a first distillation tower I. From the topmost portion of the distillation tower I is discharged a gas consisting essentially of residual propylene. The gas thus discharged is passed through line 11 to join with gas streams coming through lines 7 and 9, and may, if desired, be returned through line 19 and through line 21, respectively to line 1 through which fresh propylene is to be fed. Liquid consisting essentially of unreacted isopropyl alcohol discharged from the bottom of the distillation tower I may be, if desired, returned for recycle through line 20 and then line 22 directly to the line 2 through which fresh isopropyl alcohol is to be fed. Liquid fluid consisting essentially of the azeotropic mixture of isopropyl alcohol, diisopropyl ether and water is taken out from an upper portion of the distillation tower I (that portion located at a level higher than the middle stage of the tower) and then introduced through line 13 into rinsing tower J (a tower for contacting the liquid fluid with solvent), so that the liquid will be associated with water (solvent) coming through line 14. Unreacted isopropyl alcohol is shifted to the water phase. Liquid fluid which is taken out from the bottom of the rinsing tower J contains water and isopropyl alcohol and is discharged through line 16 to the exterior of the apparatus. Liquid fluid which is taken out from the top of the rinsing tower J is diisopropyl ether containing substantially no isopropyl alcohol and introduced through line 15 into a second distillation tower K. From the top of the distillation tower K, liquid fluid containing the azeotropic components, water and diisopropyl ether, is discharged through line 17 to the exterior, while diisopropyl ether of high purity is taken out as a product from the bottom of the distillation tower K.

Examples will be given for better understanding of the features of the present invention.

EXAMPLE 1

Diisopropyl ether was continuously produced according to the below-described procedures.

500 l of a styrene type cation-exchange resin (Amberlyst 15 having a mean grain diameter of 1 mm approximately, a product of Rohm and Hass Company) was charged as catalyst in the reaction tower C, and 100 l of hydrotalcite ($6MgO.Al_2O_3.CO_2.12H_2O$, a mean grain diameter of 0.7 mm) was charged in the neutralizing tower D. Propylene having a purity of more than 99% was fed through the line 1 at a flow velocity of 34.0 kg/hr and isopropyl alcohol having a purity of 99.9% was fed through the line 2 at a flow velocity of 55.0 kg/hr to the reaction system. In this case, propylene and isopropyl alcohol coming through line 21 and 22 join with fresh propylene and and isopropyl alcohol. The flow rate of fresh propylene entering line 1 was 151 kg/hr. (3.6 kg mole/hr.) and of fresh isopropyl alcohol introduced through line 1 was 215 kg/hr (3.58 kg mole/hr.). The pressure within the reaction system was maintained at 40 kg/cm$^2$G. The starting materials thus mixed were introduced together with fluid coming through the recycling line 4, through the line 3 into the reaction tower C. The temperature at the entrance of the reaction tower C was controlled by the heat exchanger A so as to be maintained at 105° C. The recycle flow rate of the fluid in line 4 was controlled by the recycling pump B to be 5 times as great as the rate of flow of fluid running through the line 5 (this latter rate being equal to the rate at which starting materials were fed). The flow rate of the fluid from the reaction tower C passing through the line 5 was 366 kg/hr. The fluid contained 32.9% by weight of propylene, 47.0% weight of isopropyl alcohol and 20.1% by weight of diisopropyl ether. The concentration of acid in the fluid was $1.5 \times 10^{-2}$ eq/l. The fluid leaving neutralizing tower D was introduced through line 6 into the first flashing tower F in which the pressure was maintained at 14 kg/cm$^2$G. From the top of the flashing tower F, gaseous fluid consisting essentially of 85.9% by weight of propylene and the rest consisting of isopropyl alcohol and a small quantity of diisopropyl ether was flashed at a flow rate of 81.1 kg/hr. The fluid removed from the bottom of the flashing tower F was cooled in the heat exchanger G, and thereafter introduced by way of line 8 into the second flashing tower H. From the top of the flashing tower H, a stream consisting essentially of 76.9% by weight of propylene and the rest consisting of isopropyl alcohol and a small quantity of diisopropyl ether was flashed at a flow rate of 50.3 kg/hr, while liquid taken out from the bottom of said tower was introduced into the first, 25-stage distillation tower I. The liquid fluid being introduced into the distillation tower I contained 67.5% by weight of isopropyl alcohol, 27.4% by weight of diisopropyl ether and a small quantity of propylene, and was $1.3 \times 10^{-7}$ eq/l in concentration of acid. From the topmost portion of the distillation tower I, propylene was discharged at a flow rate of 12.0 kg/hr, while unreacted isopropyl alcohol was taken out from the bottom of said distillation tower I at a flow rate of 151.1 kg/hr. Streams of gas flashed out of the tops of the respective flashing towers F, H, and discharged from the distillation tower I join with one another, and part of the streams of fluid thus joined was flashed to the exterior of the reaction system, while the remaining part was streamed through the line 21 to join with the stream of fresh propylene, which is a starting material. Isopropyl alcohol taken out from the bottom of the distillation tower I was partly discharged to the exterior of the reaction system, while the other part was streamed through the line 22 to join with the stream of fresh isopropyl alcohol which is a starting material. From the upper portion (from the fifth stage as counted from above) of the distillation tower I, the liquid fluid containing 12.2% by weight of isopropyl alcohol and 87.8% by weight of diisopropyl ether was taken out at a flow rate of 71.2 kg/hr, and the fluid thus taken out was introduced through the line 13 into the rinsing tower J, into which water was charged through the line 14 at a rate of 200 kg/hr. In the rinsing tower J, the fluid containing the mixture of isopropyl alcohol and diisopropyl ether was rinsed, and an aqueous solution containing isopropyl alcohol was discharged from the bottom of the tower to the exterior of the apparatus. The liquid fluid taken out from the top of the rinsing tower J contained 96.3% by weight of diisopropyl ether and 3.6% by weight of water. That fluid was introduced through the line 15 into the second distillation tower K. In the distillation tower K, the fluid containing the mixture of diisopropyl ether and water was subjected to distillation, and diisopropyl ether having a purity of 99.9% by weight was taken out from the bottom of said distillation tower at a flow rate of 62.5 kg/hr.

It has been found that where no neutralizing tower is provided in the apparatus shown, severe decomposition of diisopropyl ether occurs in the distillation tower I, and therefore a flow rate of diisopropyl ether which is taken out from the tower through the line 18 is as low as 11.7 kg/hr.

EXAMPLE 2

As a catalyst in the reaction tower C, there was used 500 l of sulfonated resin having a grain diameter of 20 to 50 mesh, said resin being obtained by polymerizing styrene containing about 10% of divinylbenzene and having a grain size of 20 to 50 mesh. Propylene was fed through the line 1 at a flow rate of 50.5 kg/hr. and isopropyl alcohol was fed through the line 2 at a flow rate of 94.0 kg/hr. to the reaction system. The temperature at the entrance of the reaction tower C was controlled by the heat exchanger A at 120° C. Other procedures were the same as in Example 1. The fluid coming out of the reaction tower C and passing through the line 5 contained 28.5% by weight of propylene, 35.8% by weight of isopropyl alcohol, 35.0% by weight of diisopropyl ether and 0.7% by weight of water, and was $7.2 \times 10^{-2}$ eq/l in concentration of acid. The liquid fluid introduced into the distillation tower I was $1.1 \times 10^{-7}$ eq/l in concentration of acid. From the bottom of the distillation tower K, diisopropyl ether of 99.8% by weight in purity was taken out at a flow rate of 102.5 kg/hr.

It will thus be seen that the objects set forth above, among those made apparent from the preceding description, are efficiently attained and, since certain changes may be made in carrying out the above process without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. In a process for continuously producing diisopropyl ether of high purity from isopropyl alcohol and propylene at a high yield, the improvements comprising the steps of:

passing continuously isopropyl alcohol and propylene at a molar ratio of 1:0.5 to 1:3, of isopropyl alcohol to propylene, through a first fixed bed filled with particles of strongly acidic cation-exchange resin having a mean grain diameter of 0.5 to 10 mm at a liquid space velocity of 0.2 to 2 (1/hr) at a temperature from over 100° C. to 130° C. at a pressure ranging from 20 to 50 atmospheres to react with each other;

dividing the resultant reaction mixture emerging from said first fixed bed into first and second streams;

passing said first stream through a second fixed bed filled with a water-insoluble, solid, particulate, acid-neutralizing agent having a mean grain diameter of 0.1 to 10 mm, at a temperature ranging from 20° to 130° C., said acid-neutralizing agent being selected from the group consisting of MgO, $MgO.mH_2O$ (m=0 to 0.5), $Al_2O_3$, hydrotalcite $(6MgO.Al_2O_3.CO_2.12H_2O)$, $Al_2O_3.mSiO_2.nH_2O$ (m=0.5 to 3, n=1 to 6), $Al_2O_3.nH_2O$ (n=1 to 6), $2.5MgO.Al_2O_3.nH_2O$ (n=1 to 6), $Na_2O.Al_2O_3.nH_2O$ (n=1 to 6), and $2MgO.6SiO_2.nH_2O$ (n=1 to 6);

recycling said second stream to said first fixed bed filled with said cation-exchange resin;

introducing the resultant neutralized mixture from said second fixed bed into a flashing tower and flashing the mixture to remove unreacted propylene from said mixture;

distilling the flashed mixture in a multi-stage distillation tower to recover unreacted isopropyl alcohol from the bottom of said distillation tower and obtain an azeotropic mixture comprising isopropyl alcohol and diisopropyl ether from an upper portion of said distillation tower;

bringing said azeotropic mixture comprising isopropyl alcohol and diisopropyl ether into contact with a solvent selected from the group consisting of hydrocarbons, water and lower alcohols having from 1 to 4 carbon atoms, thereby separating said azeotropic mixture into a layer of isopropyl alcohol and a layer of diisopropyl ether, said layer of isopropyl alcohol containing said solvent when said solvent is water or the lower alcohol, and said layer of diisopropyl ether containing said solvent when said solvent is hydrocarbons;

separating said layers; and distilling said layer of diisopropyl ether, whereby diisopropyl ether of high purity is obtained.

2. The improvement in the process as defined in claim 1, wherein a stream consisting essentially of propylene is recovered from the top of said flashing tower and any subsequent flashing towers and is recycled to said first fixed bed of cation-exchange resin.

3. The improvement in the process as defined in claim 1 wherein a stream consisting essentially of isopropyl alcohol is recovered from said multi-stage distillation tower and is recycled to said first fixed bed of cation-exchange resin.

4. The improvement in the process as defined in claim 1, wherein a ratio in quantity of fresh isopropyl alcohol and propylene to be fed to said first bed to said second stream to be recycled is from 1:3 to 1:10 by weight.

* * * * *